United States Patent

Asai et al.

[11] Patent Number: 5,120,460
[45] Date of Patent: Jun. 9, 1992

[54] DENTAL CLEANER MATERIALS

[75] Inventors: Yasuhiro Asai, No. 14-3, Nakamachi 2-chome, Setagaya-ku, Tokyo; Kiyoko Nakamura, Tokyo; Masayuki Takahashi, Misato, all of Japan

[73] Assignees: G-C Dental Industrial Corp.; Yasuhiro Asai, both of Tokyo, Japan

[21] Appl. No.: 501,960

[22] Filed: Mar. 29, 1990

Related U.S. Application Data

[63] Continuation of Ser. No. 223,080, Jul. 22, 1988, abandoned.

[30] Foreign Application Priority Data

Aug. 12, 1987 [JP] Japan .................. 62-199882

[51] Int. Cl.$^5$ .................. A61K 7/22; C11D 3/30; C11D 3/37; C11D 3/48
[52] U.S. Cl. .................. 252/106; 252/174.23; 252/174.24; 252/546; 252/DIG. 11; 424/49; 424/54; 424/55; 433/215; 433/216; 514/546
[58] Field of Search .......... 252/106, DIG. 11, 174.23, 252/174.24, 546; 433/215, 216; 424/49, 54, 55; 514/546

[56] References Cited

U.S. PATENT DOCUMENTS

| | | | |
|---|---|---|---|
| 3,087,857 | 4/1963 | Davis et al. | 424/55 |
| 4,251,507 | 2/1981 | Olson | 424/55 |
| 4,357,318 | 11/1982 | Shah et al. | 424/49 |
| 4,363,794 | 12/1982 | Ochiai et al. | 424/49 |
| 4,457,909 | 7/1984 | Tamés | 424/49 |
| 4,485,029 | 11/1984 | Kato et al. | 514/912 |
| 4,610,872 | 9/1986 | Lynch | 424/49 |
| 4,807,649 | 2/1989 | Eoga | 134/2 |
| 4,847,070 | 7/1989 | Pyrz et al. | 424/57 |
| 4,850,872 | 7/1989 | Goldman et al. | 433/215 |
| 4,978,522 | 12/1990 | Barbera et al. | 424/52 |
| 5,032,388 | 7/1991 | Tikkanen | 424/49 |

FOREIGN PATENT DOCUMENTS 0040738 12/1981 European Pat. Off. .

OTHER PUBLICATIONS

Jodaikin et al *J. Prosth. Dentistry* vol. 46, No. 2 Aug. 1981, pp. 171–174.
Lindemann et al *J. Prosth. Dentistry* vol. 53 Mar. 1985 pp. 341–343.
Meryon et al, *J. Prosth. Dentistry* vol. 57, No. 2 Feb. 1987 pp. 174–179.
Brannstrom et al, CA (93)(18):173705g from *J. Dent Res.* 59(7), 1127-31 1980.
CA 96(6):40856x.
CA 104(10):74987q (1985).
CA 109(10):79682z (1988).
Brannstrom et al *J. Dent. Res.* vol. 59 No. 7 Jul. 1980 pp. 1127–1131.
Jodaikin et al *Journal of the Dent. Assoc. of South Africa* vol. 36 Sep. 1981 pp. 615–617.
Meryon et al *Endod. Dent. Traumatol.* vol. 4 No. 3 1988 pp. 118–121.
Wendt et al *Dent Mater* Jan. 1990 vol. 6 (1) Abstract Only.
Mason et al *G. Stomatol Ortognatodonzia* Jul.–Sep. 1987 6(3) Abstract Only.
Chemical Abstract CA106(21):172814s; Russell et al *Int. J. Pharm* 35(3) pp. 227–233 1987.

*Primary Examiner*—A. Lionel Clingman
*Assistant Examiner*—Linda D. Skaling
*Attorney, Agent, or Firm*—Oblon, Spivak, McClelland, Maier & Neustadt

[57] ABSTRACT

A dental cleaner material comprises as a main component an aqueous solution containing 0.1 to 2.0% by weight of ethylenediaminetetraacetic acid or at least one of its alkali metal salts. The cleaner material is gelled by the addition of a carboxyvinyl polymer, carboxymethylcellulose or sodium carboxymethylcellulose as a raiser in viscosity showing thixotropy, further contains 0.01 to 0.3% by weight fo a p-hydroxybenzoic acid ester as an antibacterial agent, and is regulated to pH of 7.0±0.5.

2 Claims, No Drawings

DENTAL CLEANER MATERIALS

This application is a continuation of application Ser. No. 07/223,080, filed on Jul. 22, 1988, now abandoned.

BACKGROUND OF THE INVENTION

1. Field of the Invention

The present invention relates to a dental cleaner material for removing a smear layer formed during cutting without injuring the tissue of a dentinal region, inter alia, dentine and, more particularly, to a cleaner material for cleaning cavities or the root canals.

2. Prior Art

In the preparation of a cavity in conservative dentistry, a dentinal region is partly cut away by dental abrasive materials such as diamond points or tungsten carbide bars. In this case, a part of dentine in the cavity is deposited onto the surface of dentine in the form of a layer comprising finely divided dentinal chips to form a deposit layer called the "smear layer". Such dentinal chips also enter into dentinal tubules and form dentinal plugs to close them up. Such a smear layer is said not only to mar the effect of pharmaceuticals applied thereto but also to lower the adhesion of a restorative material such as a composite resin to the dentinal region.

Due to difficulty encountered in the mechanical removal of the smear layer from within cavities with the use of a dental instrument, they have heretofore been eliminated by dissolving it in a dental etching material such as an aqueous solution of phosphoric or citric acid.

The smear layer is also found to be formed during the preparation of the root canal in endodontics by mechanical cutting with reamers, files or the like. The smear layer deposited onto the inner wall of the root canal contains therein residual pulpal tissue pieces and their decayed products as well as pus and microorganisms and their products, etc., which stimulate the tissue of the root canal end or mar the permeability and pharmacological effect of pharmaceuticals applied into the root canal, and further lower the adherence of a root canal filler to the root canal wall. In order to clean the interior of the root canal having its inner wall covered with such a smear layer, use has heretofore been made of pharmaceutical formulations based principally on sodium hypochlorite, phenol sulfonate and ethylenediaminetetraacetic acid (hereinafter abbreviated as "EDTA") as well as aqueous hydroxide peroxide.

When an aqueous solution of phosphoric or citric acid is used as the cavity cleaner, however, not only the smear layer deposited onto dentine but also the sound or healthy residual dentine are so dissolved therein that the cut ends of dentinal tubules are enlarged in the form of a funnel, and even collagen may be denatured by its strong acidity. The results are that the hypersensitivity of the dental pulp is induced; the monomer remaining in a composite resin or bacteria enter into the tubules; and the remaining sound dentine is too weakened to degrade the adherence of a restorative material.

Most of commercially available dental etching materials comprise an aqueous solution of phosphoric or citric acid to which highly dispersible silica (e.g., Aerosil R-380 manufactured by Nippon Aerosil Co., Ltd.) is added as a thixotropic material to improve workability, and there is a liklihood that highly dispersible silica particles may remain on the surface of the dentinal region, resulting in a lowering of the adherence of a restorative material, unless they are removed in water washing as carefully as possible.

Similarly, the smear layer is formed during the preparation of the root canal in endodontics. Such a layer has been removed by using mixed formulation of sodium hypochlorite with sodium hydroxide, about 10% aqueous solution of sodium hypochlorite, about 15% aqueous solution of EDTA, fomulation based principally on phenol sulfonate, aqueous hydroxide peroxide or the like. However, the mixed formulation comprising sodium hypochlorite and sodium hydroxide or about 10% aqueous solution of sodium hypochlorite may dissolve bacteria and the intra-root canal decayed products that are organic matters, but fail to dissolve the smear layer composed primarily of inorganic deposits. Further, about 15% aqueous solution of EDTA dissolve not only the smear layer but also sound dentine. Still further, careful attention should be paid to the use of phenol sulfonate formulations, since, although weaker than inorganic acids, they are acid so strong that they tend to be deposited onto parodontium (or soft tissue).

SUMMARY OF THE INVENTION

The present invention has been made for the purpose of solving the problems of the prior art, and is concerned with a dental cleaner material for removing or eliminating a smear layer deposited onto the surface of dentine without injuring dentinal tubules.

According to the present invention, therefore, there is provided a dental cleaner material containing an aqueous solution of EDTA or its alkali metal salt or salts as a main component, a p-hydroxybenzoic acid ester as an antibacterial agent and a carboxyvinyl polymer, carboxymethylcellulose or sodium carboxymethylcellulose as a raiser in viscosity showing thixotropy, said material being adjusted to pH = 7.0 ± 0.5.

DETAILED DESCRIPTION OF THE INVENTION

In accordance with the present invention, it is possible to remove a smear layer deposited onto the surface of dentine and capable of providing a culture medium for bacteria, thereby safely conserving dentinal tubules; sterilize sound dentine and partly remaining dentinal plugs; and enhancing a pharmacological effect upon dentine and further the dental pulp. More specifically, it has been found that in order to remove the smear layer deposited onto the surface of dentine and conserve dentinal tubules in a state as close to a physiological state as possible, the concentration of an aqueous solution of EDTA or its alkali metal salt or salts should suitably be 0.1 to 2.0% by weight. Further, a p-hydroxybenzoic acid ester expressed by the following general formula:

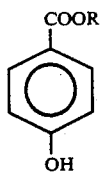

wherein R stands for an alkyl group having 1 to 4 carbon atoms, is added to that aqueous solution as an antibacterial agent for sterilizing sound dentine and partly remaining dentinal plugs through its strong bacteriostasis. Still further, the aqueous solution of EDTA or its alkali metal salt or salts is regulated to a pH region of 7.0±0.5, and a water-soluble high polymer exhibiting strong thixotropy in such a pH region, i.e., a carboxyvinyl polymer, carboxymethylcellulose or sodium carboxymethylcellulose is added in an amount of 0.01 to 10 parts by weight with respect to 100 parts by weight thereof to improve its workability and make its application to the interiors of cavities or the root canals easy. By doing so, that aqueous solution can be applied to cavities or the root canals in every direction, while allowing the required amount thereof to sojourn in the required sites of such cavities or the root canals. Unlike the conventional dental etching materials increased in viscosity as by highly dispersible silica, the present aqueous solution can easily be removed even by water washing without any residue, since it is thickened by the water-soluble high polymer.

The dental cleaner material according to the present invention exerts a sufficient cleaning effect upon the smear layer, while it gives only limited stimuli, and is very mild, with respect to the internal soft tissue of the dentinal region or dentine. In other words, the present cleaner material is suitable as both a cavity cleaner and a root-canal cleaner, and meets the fundamentals of dentistry that injuries to the sound dentine should be as much reduced or prevented as possible.

In the present invention, the concentration of EDTA or its alkali metal salt or salts should suitably be in a range of 0.1 to 2.0% by weight. Concentrations lower than 0.1% by weight are practically unsuitable, since such lower concentrations have a reduced cleaning effect upon the smear layer. Concentrations higher than 2.0% by weight are unsuitable as the dental cleaner material required to give no injury to dentine, since such higher concentrations cause not only the smear layer but also healthy dentine to be dissolved to such an extent that the cut ends of dentinal tubules are enlarged in the form of a funnel.

The p-hydroxybenzoic acid ester to be added as an antibacterial agent is suitably in a concentration range of 0.01 to 0.3% by weight, and butyl, propyl, ethyl and methyl esters may be used alone or in combination. Concentrations lower than 0.01% by weight or higher than 0.3% by weight are practically unsuitable, since such lower concentrations may not exert any sufficient bacteriostasis with respect to bacteria contained in the smear layer, while such higher concentrations make it difficult to dissolve that agent in water.

The concentration of a carboxyvinyl polymer, carboxymethylcellulose or sodium carboxymethylcellulose added as the thixotropic material should suitably be in a range of 0.01 to 10 parts by weight per 100 parts by weight of the aqueous solution of EDTA or its alkali metal salt or salts. Concentrations lower than 0.01 part by weight are practically unsuitable, since the resulting cleaner material is poor in thixotropy and give rise to "dripping" when applied to an angular cavity and hence a lowering of workability. Concentrations higher than 10 parts by weight are again practically unsuitable, since the resulting cleaner material is so increased in viscosity and poor in flowability that difficulty is encountered in its application into the root canal.

EXAMPLES

The present invention will now be explained with reference to the following examples; it should be borne in mind, however, that the present invention is not limited thereto.

Each of the dental cleaners was evaluated in the following manner. The dental cleaner was applied to a cavity and the root canal, both formed in a pulled-out tooth, for one minute, followed by water washing. The tooth was dried by an air syringe to observe the cleaning effect under a scanning electron microscope.

EXAMPLE 1

Cavity Cleaner

2Na-EDTA—0.3% by weight
Purified water—99.18
Butyl p-hydroxybenzoate—0.02
Carboxyvinyl polymer—0.5
were regulated to pH=7.0 with a 10% aqueous solution of sodium hydroxide.

EXAMPLE 2

Root-Canal Cleaner

2Na-EDTA—1.0% by weight
Purified water—98.96
Butyl p-hydroxybenzoate—0.02
Carboxyvinyl polymer—0.02
were regulated to pH=7.0 with a 10% aqueous solution of sodium hydroxide.

EXAMPLE 3

2Na-EDTA—0.15% by weight
4Na-EDTA—0.15
Purified water—96.53
Ethyl p-hydroxybenzoate—0.15
Butyl p-hydroxybenzoate—0.02
Carboxymethylcellulose—3.0
were regulated to pH=7.0 with a 10% aqeuous solution of sodium hydroxide.

EXAMPLE 4

A composition of Example 2, provided that 3Na-EDTA was used in place of 2Na-EDTA.

EXAMPLE 5

A composition of Example 2, provided that 4Na-EDTA was used in place of 2Na-EDTA.

COMPARATIVE EXAMPLE 1

Commercially available dental etching material (40% aqueous solution of phosphoric acid increased in viscosity by highly dispersible silica).

COMPARATIVE EXAMPLE 2

3% sodium hypochlorite solution (dental antiformine).

COMPARATIVE EXAMPLE 3

2Na-EDTA—0.05% by weight
Purified water—99.43
Butyl p-hydroxybenzoate—0.02
Carboxyvinyl polymer—0.5
were regulated to pH=7.0 with a 10% aqueous solution of sodium hydroxide.

COMPARATIVE EXAMPLE 4

A dental cleaner having a similar composition to that of Comparative Example 3, provided that 2Na-EDTA was used in an amount of 2.5% by weight.

COMPARATIVE EXAMPLE 5

2Na-EDTA—0.3% by weight

Purified water—87.68
Butyl p-hydroxybenzoate—0.02
Carboxyvinyl polymer—12
were regulated to pH=7.0 with a 10% aqueous solution of NaOH.

COMPARATIVE EXAMPLE 6

A composition of Comparative Example 5, from which the carboxyvinyl polymer was removed.

| | Results of Testing | | | |
|---|---|---|---|---|
| | Removal of Smear Layer | Condition of Dentine | Work-ability | Removal of Residue |
| Example 1 | ○ | ○ | ○ | ○ |
| Example 2 | ○ | ○ | ○ | ○ |
| Example 3 | ○ | ○ | ○ | ○ |
| Example 4 | ○ | ○ | ○ | ○ |
| Example 5 | ○ | ○ | ○ | ○ |
| Comparative Example 1 | ○ | X | ○ | X |
| Comparative Example 2 | X | ○ | X | ○ |
| Comparative Example 3 | X | ○ | ○ | ○ |
| Comparative Example 4 | ○ | Δ | ○ | ○ |
| Comparative Example 5 | ○ | ○ | X | X |
| Comparative Example 6 | ○ | ○ | X | ○ |

○: Good
Δ: Somewhat Bad
X: Bad

EFFECT OF THE INVENTION

The present invention provides a dental cleaner material which contains as its main component an aqueous solution of EDTA or its alkali metal salt or salts, and is regulated to pH=7.0±0.5 that gives no stimuli to dental pulp or periapical tissues. This cleaner material makes it possible to safely clean the interior of a cavity or the root canal without anxiety and injuring a dentinal region, especially, dentine. Further, the addition of the antibacterial agent makes it possible to simultaneously sterilize the interiors of cavities and the root canals during cleaning. Still further, the present cleaner is suitably gelled by the addition of the thixotropic material, and is thus applicable to any kinds of cavities and the root canals, while maintaining its sojourn.

When the dentinal chip-deposited layer (the smear layer) formed by mechanical cutting are cleaned out with the dental cleaner material having the aforesaid effect, it is possible to conserve the cut ends of dentinal tubules in a state close to a physiological state. It is thus said that the present invention serves to enhance the effect of pharmaceuticals applied into cavities or the root canals and is of use for the dental treatment for conserving healthy dentine.

What is claimed is:

1. A smear layer removing composition consisting essentially of an aqueous solution containing 0.1 to 2.0% by weight of ethylenediaminetetraacetic acid or at least one of its alkali metal salts, 0.01% to 10% by weight of a carboxyvinyl polymer which thixotropically gels said solution, 0.01 to 0.3% by weight of an antibacterial agent, about 87.7-99.88% water and a pH regulating agent in an amount sufficient to bring the pH to 7.0±0.5.

2. A smear layer removing composition as claimed in claim 1, wherein said antibacterial agent is a p-hydroxybenzoic acid ester expressed by the following general formula:

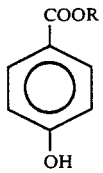

wherein R stands for an alkyl group having 1 to 4 carbon atoms.

* * * * *